United States Patent [19]
Citron

[11] 3,978,148

[45] Aug. 31, 1976

[54] PROCESS FOR REMOVAL OF RHODIUM COMPOUNDS FROM PROCESS STREAMS

[75] Inventor: Joel David Citron, Wilmington, Del.

[73] Assignee: E. I. Du Pont de Nemours and Company, Wilmington, Del.

[22] Filed: July 21, 1975

[21] Appl. No.: 597,492

[52] U.S. Cl. .................. 260/680 B; 252/411 R; 260/681.5 R; 423/22
[51] Int. Cl.² .......................................... C07E 11/12
[58] Field of Search .......... 260/681.5, 680; 423/22; 252/411, 444

[56] References Cited
UNITED STATES PATENTS

| | | | |
|---|---|---|---|
| 3,360,134 | 12/1967 | Pullen | 210/502 |
| 3,433,358 | 3/1969 | Herzog et al. | 210/65 |
| 3,694,370 | 9/1972 | Panesko | 423/22 |
| 3,755,152 | 8/1973 | Gulick | 208/307 |
| 3,845,154 | 10/1974 | Keller | 260/680 B |
| 3,848,048 | 11/1974 | Moore | 423/22 |
| 3,855,396 | 12/1974 | Kniese et al. | 423/22 |

FOREIGN PATENTS OR APPLICATIONS

| | | | |
|---|---|---|---|
| 1,518,305 | 3/1968 | France | 423/22 |

*Primary Examiner*—Veronica O'Keefe

[57] ABSTRACT

Dissolved rhodium compounds are removed from liquid, organic process streams in the manufacture of 1,4-hexadiene from 1,3-butadiene and ethylene by contacting the organic process streams with activated carbon of decolorizing grade for at least about 0.1 hour at about −20° to +120°C. The adsorbed rhodium can be recovered at a reasonable cost and reused. This invention thus provides an economic incentive.

11 Claims, No Drawings

PROCESS FOR REMOVAL OF RHODIUM COMPOUNDS FROM PROCESS STREAMS

BACKGROUND OF THE INVENTION

This invention relates to a process for the recovery of soluble rhodium compounds from the organic phase of spent process streams in the preparation of 1,4-hexadiene from ethylene and 1,3-butadiene. 1,4-Hexadiene is a valuable monomer for use in manufacturing sulfur-curable EPDM rubber.

U.S. Pat. No. 3,845,154 (to W. J. Keller) describes a typical 1,4-hexadiene manufacturing process that would be benefited by the present invention. In the process of U.S. Pat. No. 3,845,154, ethylene and 1,3-butadiene are contacted in the presence of a rhodium catalyst in a poly (oxyethylene) ether solvent, usually at about 50°–100°C. and 100–700 psig. The reactor effluent contains 1,4-hexadiene, solvent, rhodium catalyst, various $C_8$–$C_{12}$ by-products, and unchanged starting materials. Low-boiling materials (ethylene, 1,3-butadiene, and 1,4-hexadiene) are flashed off. The residual high-boiling liquid contains the polyether solvent, rhodium catalyst, and the high-boiling $C_8$–$C_{12}$ by-products. A portion of this residual material is diverted, while the bulk is recycled to the reactor. The purpose of this diversion is to prevent accumulation of the undesirable high boilers. Valuable polyether solvent is recovered by water extraction of the diverted material.

Rhodium catalyst should be removed from that diverted portion of the liquid for economic reasons. This can be done, for example, by burning the high boiling by-products, but the low concentration of rhodium (e.g., 300–1800 ppm) necessitates undesired handling of large volumes of liquid. In the event of a plant shutdown, it is particularly important to be able to recover rhodium from the whole process stream before the latter is discarded.

There is a need, therefore, for a simple method of recovery of soluble rhodium compounds from the reactor effluent.

SUMMARY OF THE INVENTION

The present invention provides a process for the removal of rhodium compounds dissolved in an organic, liquid effluent from a process in which 1,4-hexadiene is made from ethylene and 1,3-butadiene, wherein the organic, liquid effluent is first contacted for at least about 0.1 hour with activated carbon of decolorizing grade, then separated from the activated carbon.

DETAILED DESCRIPTION OF THE INVENTION

Rhodium compounds which are useful in the 1,4-hexadiene manufacturing process are taught in U.S. Pat. Nos. 3,013,166 (Alderson), 3,152,195 (Verbanc), 3,502,738 (Cramer), 3,565,821 (Su), and 3,640,898 (Su). In general, any Rh(I) or Rh(III) compound which can be solubilized under the reaction conditions and from which active catalyst species can be generated is suitable. A preferred Rh(III) compound which can be converted to an active species by interaction with hydrochloric acid, ethylene, and 1,3-butadiene is $RhCl_3 \cdot 3H_2O$. A detailed mechanism for this conversion has been put forth by R. Cramer, J. Am. Chem. Soc., 89, 1633 (1967). Active catalyst species can be generated from Rh(III) compounds, such as Rh(acetylacetonate)$_3$, [($CH_3$—CH=CH—$CH_2$)$_2$RhCl]$_2$, $RhF_3 \cdot 6H_2O$, $RhBr_3$, Rh(CN)$_3 \cdot 3H_2O$, $Rh_2(SO_4)_3$, $RhI_3$, $Rh_2(CO_3)_3$, and Rh(NO$_3$)$_3$, when they are used with water and HCl in the presence of ethylene and butadiene.

Rh(I) compounds will not catalyze the formation of 1,4-hexadiene from ethylene and 1,3-butadiene unless they are activated. Further, during the reaction of ethylene with 1,3-butadiene, some of the rhodium catalyst becomes deactivated. Activation and reactivation are taught in U.S. Pat. No. 3,152,195 (Verbanc), which uses HCl, and U.S. Pat. No. 3,565,821 (Su), which uses agents such as chlorine, carbon tetrachloride, carbon tetrabromide, or an organic compound having an active chlorine or bromine atom attached to a carbon atom joined directly to a vinyl, substituted vinyl, phenyl, substituted phenyl, cyano, or carbonyl radical, or an α-chloroether oxygen atom. Examples of these agents include benzotrichloride, hexachloroacetone, allyl chloride, chloroprene, and N,N-diethyl trichloroacetamide.

While the nature of the active catalytic species is not known with certainty, it is believed that under the conditions of the 1,4-hexadiene synthesis from ethylene and 1,3-butadiene, substantially the same catalytic species is formed in situ whenever rhodium compound is initially used as the catalyst.

Decolorizing-grade activated carbon suitable in the process of this invention is well known in the trade and is to be distinguished from the water-purifying grade of activated carbon. A good source of general information concerning activated carbon and processes in which activated carbon can be used is a book entitled, "Purification With Activated Carbon", by John W. Hassler, Chemical Publishing Co., Inc., New York, N.Y., 1974. Activated carbon can be produced from a variety of starting materials, including carbohydrates, bones, coal, wood, lampblack, petroleum coke, and pulpmill waste, to name a few. Since no definite structural formula or chemical analysis can properly characterize any grade of activated carbon, it is accepted to distinguish each grade or type by its adsorptive or catalytic properties. The decolorizing properties of activated carbon are usually measured by adsorption of "standard" substances, such as dyes, or standard impurities. Surface area and pore size distribution measurement techniques are discussed in *Bibliography of Solid Adsorbents*, by V. R. Dietz, U.S. Cane Sugar Refiners and Bone Char Manufacturers, and the National Bureau of Standards, Washington, D.C., 1944, supplementary volume issued in 1956. Usually, the characteristics of each commercial activated carbon can be obtained from the manufacturer. It is generally believed that decolorizing grade activated carbons have a substantial porportion of large size pores.

Although one practicing the present invention will usually rely on the active carbon manufacturers' designations, one occasionally may need to determine whether a given activated carbon would be suitable in the present process. One way to ascertain it would be by actual rhodium removal tests under the conditions of this invention. However, one can use for the preliminary screening a standard molasses decolorization test described in the above-cited Hassler's book. Depending on the type of molasses, an aqueous solution containing about 20–60 grams of molasses per liter and having a pH of 6.5 is prepared. A 50 ml. portion of the solution is stirred with 0.5 gram of carbon, heated to boiling, and filtered. The color of the filtrate is measured, and the determination is repeated if necessary with larger or smaller amounts of the carbon, until 70–90% of color is removed. An alternative but similar technique requires shaking in a steam chest for 50 minutes, then shaking for additional 45 minutes without heating before filtration.

The efficiency of color removal is compared with that of a standard decolorizing carbon having known properties. Good decolorizing grade activated carbons will remove a substantial amount of colored impurities from a solution of molasses under the test conditions and will have a good color removal efficiency on weight basis. While the test is relative, rather than absolute, it is generally used in the trade and can be interpreted by those skilled in the art without difficulty.

Before the reactor liquid effluent is used in the process of this invention, it is preferred that volatiles (for example, ethylene, 1,3-butadiene, 1,4-hexadiene, water, and HCl) be substantially removed. It is convenient to direct the reactor liquid effluent to a conventional flash chamber operated at subatmospheric pressure. Volatiles exit overhead to conventional scrubbers and fractionation means for separating and recovering 1,4-hexadiene. Typically, the flasher will be maintained at 75°–95′C. and 0.21–0.56 kg./cm.$^2$ (absolute). Flasher liquid effluent, exiting at or near the bottom of the flasher, subsequently passes through a heat exchanger where it is cooled slightly below reaction zone temperature, and finally enters a pump which delivers it into the reactor recycle feed line for reuse in the system.

It should be understood that the process of the present invention is not limited to the workup of organic liquids from the above-cited Keller process. Other organic liquids which can be used in the synthesis of 1,4-hexadiene from ethylene and 1,3-butadiene may be present in the solutions which can be treated according to the present invention. A high-boiling mineral oil, for example, can be such an organic liquid.

In the process of the present invention, it is important to assure good contact of the organic liquid with the activated carbon for the best efficiency of rhodium residue removal. This can be accomplished by several techniques. The simplest technique involves passing the liquid stream through a stationary bed of activated carbon in a manner similar to ordinary column chromatography. It also is possible to remove the rhodium compounds continuously in a countercurrent arrangement, wherein the liquid from the reactor flows in one direction, while the activated carbon in the organic liquid flows in the opposite direction in such manner that both streams come in intimate contact. This general procedure was recommended as early as 1923, by M. T. Sanders, in Ind. Eng. Chem. 15, 784 (1923).

A practical embodiment of countercurrent application involves a moving bed operation in a single column. The flow of liquid is directed upward through the bed of activated carbon, while the carbon advances periodically down through the column. At definite time intervals, a small amount of spent carbon is removed from the bottom, while fresh carbon is added through the top. This technique is outlined in the above-cited book of John W. Hassler.

Another technique described in that book is a contact-batch unit operation, which requires a tank equipped with an agitator. A slurry of activated carbon in the liquid phase is agitated for the desired time, then pumped through a filter to separate the carbon from the liquid. Various other techniques can be used and can be readily adapted or designed by a skilled engineer. Filtration is a good method for separating activated carbon from the liquid phase in techniques other than percolation of the liquid through an activated carbon bed.

The activated carbon should remain in contact with the rhodium residue-containing liquid for at least about 0.1 hours. The maximum time of contact is not critical and, usually, longer contact time will permit a more complete rhodium recovery. Of course, a point in time will be reached at which further contact will not produce significant, or even any, improvement, and beyond which it would not be economically practical to operate. A practical upper limit is about 100 hours. On industrial scale, the time of contact, especially in a column arrangement, will normally be so adjusted that the normal rate of flow of the liquid from the hexadiene manufacture process will be maintained. In a given installation, a contact time of 40–70 hours may be quite practical.

The concentration of rhodium in the starting organic liquid may vary widely because of the unavoidable variations of the hexadiene manufacturing process itself from batch to batch or from run to run. A concentration of about 300–1800 ppm of the organic liquid will be encountered most frequently. It will have to be kept in mind that the amount of activated carbon which will be required to adequately recover rhodium from solution may increase as the rhodium concentration increases. While it is impossible to recommend any specific carbon-to-rhodium ratio, the necessary minimum amount of activated carbon for any given concentration of rhodium can be readily determined for each desired technique in a simple manner. The concentration of rhodium in solution can be determined approximately by colorimetric methods of more exactly by atomic absorption.

A convenient colorimetric method involves measuring the "Gardner Color" of the rhodium solutions. Standard colored solutions are visually compared with the unknown, and the unknown is given a Gardner Color Number (1 to 18). The value obtained is referred to a working curve wherein the observed Gardner Color Numbers of rhodium solutions of known rhodium concentration are plotted against the rhodium concentrations.

Atomic absorption spectrophotometry can be used as follows. A solution containing rhodium is aspirated into a flame produced by an acetylene/air mixture or acetylene/nitrous oxide mixture. The rhodium is reduced to its absorbing atomic state. Light is passed through the flame and into a monochromator which isolates a "resonance" line at 343.5 nm. The intensity of this line is measured. The decrease in intensity of the resonance line caused by the absorption of the rhodium sample is compared with adsorption produced by a standard of known rhodium concentration. A typical apparatus is the Jarrell-Ash Model 810, made by the Jarrell-Ash Division of Fisher Scientific Company.

The rhodium recovery temperature is not critical. On the low side it is limited by the freezing temperature of the solution, while on the high side by the practicality of the operation and the boiling or decomposition temperature of the liquid. Usually, there will be no advantage in operating outside a range of about −20° to +120°C. It is not certain whether or not the temperature has any influence on the efficiency of rhodium removal; however, increasing the temperature increases the fluidity of the solution and facilitates liquid or slurry circulation and pumping. No pressure range is recommended, and the process can be run conveniently at subatmospheric, atmospheric, or superatmospheric pressure.

Because the effluent from the hexadiene-manufacturing process is acidic from hydrochloric acid, it is necessary to use in the rhodium recovery process appropriate acid-resistant equipment. Materials such as tantalum, solvent-resistant plastics and resins, or glass-lined steel can be used. Similar considerations will apply when other activators are used in place of hydrochloric acid.

It is not necessary for the operability of the present invention to maintain any specific atmosphere in the rhodium recovery equipment. Nevertheless, for reasons of safety, because of the presence of residual olefinic materials in the solution, it is sometimes practical to operate under a nitrogen blanket.

Rhodium can be recovered from the spent activated carbon by various methods, including oxidation with a strong oxidizing agent, such as, for example, acidic chromium trioxide, which converts carbon to carbon dioxide, leaving rhodium in a readily available form.

This invention is now illustrated by the following examples of certain preferred embodiments thereof wherein all parts, proportions, and percentages are by weight unless otherwise indicated. Activated carbon specifications are based on manufacturers' literature.

RHODIUM SOLUTIONS

The 1,4-hexadiene recycle catalyst stream was similar to the one described in the Example in U.S. Pat. No. 3,845,154, issued to W. J. Keller. Ethylene and 1,3-butadiene were contacted in the presence of triethyleneglycol monobutyl ether to which had been added a dilute hydrochloric acid solution of $RhCl_3 \cdot 3H_2O$. 1,4-Hexadiene, ethylene, 1,3-butadiene, water vapor, and HCl were substantially removed by flashing from the reactor effluent. The resulting flasher effluent contained triethyleneglycol monobutyl ether, high-boiling $C_8$–$C_{14}$ hydrocarbon fractions (predominantly $C_{10}$)., soluble organo complexes of rhodium, and very small amounts of volatile components, such as HCl, 1,3-butadiene, and 1,4-hexadiene.

EXAMPLE 1

A 60 × 1.5 cm. column of Darco (ICI United States, Inc.) granular, decolorizing-grade activated carbon, 12 × 40 mesh, was made up. This activated carbon has a total surface area of 625 sq. meters per gram, a total pore volume of 0.95 ml./gm., and the following pore volume distribution:

| mean pore radius | ml./gm. |
|---|---|
| <35A | 0.2 |
| 35–100A | 0.3 |
| 100–1000A | 0.2 |
| >1000A | 0.3 |

The unwashed flasher effluent (containing 506 ppm of rhodium) was passed through the column at room temperature and at atmospheric pressure while exposed to air. The solution was dark red before passing through the column, and dark yellow afterwards. Atomic absorption analysis showed there was 95 ppm of rhodium in the effluent.

EXAMPLE 2

Measured amounts of two powdered decolorizing-grade activated carbons, Darco G-60 and Darco KB (ICI United States, Inc.), were mixed with 50-ml. portions of a water-washed, 1,4-hexadiene recycle catalyst solution containing 633 ppm of rhodium (as soluble organo complexes). After 5 hours of agitation at room temperature at atmospheric pressure while exposed to air, each mixture was filtered and the filtrate analyzed by atomic absorption for rhodium. The results are given below.

| | ppm rhodium | |
|---|---|---|
| gm. carbon | Darco G-60 | Darco KB |
| 0.3 | 574 | 492 |
| 0.6 | 524 | 425 |
| 1.2 | 467 | 341 |
| 2.4 | 456 | 291 |
| 4.8 | 366 | 130 |

The activated carbons had the following characteristics:

| | Darco G-60 | Darco KB |
|---|---|---|
| Total Surface Area (sq. meters per gram) | 600 | 1450 |
| Total Pore Volume (ml. per gram) | 1 | 1.5 |
| Pore Volume Distribution (ml. per gram) | | |
| <20A | 0.1 | 0.3 |
| 20–50A | 0.1 | 0.4 |
| 50–100A | 0.3 | 0.2 |
| 100–500A | 0.35 | 0.45 |
| >500A | 0.15 | 0.15 |
| Mean Pore Radius, (A) | 25 | 23 |

EXAMPLE 3

Measured amounts of three granular, decolorizing grade activated carbons CAS 400 (Calgon Corp.), Darco (ICI United States, Inc.) granular 20 × 40 mesh, and Nuchar WV-G (Westvaco, Chemical Div.), 12 × 40 mesh, were shaken for 72 hours at room temperature at atmospheric pressure while exposed to air with 50 ml. of a water-washed 1,4-hexadiene recycle catalyst solution containing 649 ppm of rhodium (as soluble organo complexes). The following results were obtained by atomic absorption analysis

| | rhodium, ppm | | |
|---|---|---|---|
| gm. carbon | CAS 400 | Darco 20×40 | Nuchar WV-G |
| 0.5 | 476 | 521 | 473 |
| 1.0 | 397 | 460 | 425 |
| 2.0 | 317 | 378 | 336 |
| 4.0 | 226 | 288 | 256 |

All the above active carbons are reasonably effective in removing the rhodium from solution.

CAS 400 has a total surface area of 1000–1200 sq. meters per gram, a total pore volume of 1.4 ml. per gram, a mean particle diameter of 1.0 mm. and an iodine number of about 1100; a maximum of about 5% is larger than sieve size 12 and a maximum of about 4% is smaller than sieve size 40. Nuchar Granular WV-G has a large number of pores between 20 and 100A in radius.

EXAMPLE 4

A column of Darco Granular decolorizing-grade activated carbon, 20 × 40 mesh, was made up by pouring 91.5 gm. of the carbon into a 50 cm. long × 2.5 cm. diameter column filled with hexane. A water-washed 1,4-hexadiene recycle catalyst solution containing 633 ppm of rhodium (as soluble organic complexes) was passed through at about 100 ml./hr. at room temperature while exposed to air. Fractions (100 ml. each) were collected, and the atomic absorption analyses for rhodium for some of them are given below.

| fraction | ppm rhodium |
| --- | --- |
| 0–100 ml. | 27 |
| 201–300 | 91 |
| 401–500 | 233 |
| 601–700 | 290 |

The increasing rhodium concentration indicates that the activated carbon was becoming saturated with rhodium. A longer or larger diameter column would have had greater capacity.

EXAMPLE 5

A slurry of 1750 gm. of Nuchar WV-G decolorizing activated carbon in hexane was poured into a 5 cm. inside diameter column. The carbon column was 1.83 meters high. Water-washed recycle catalyst solution was passed through at a rate of about 195 ml./hr.; the recycle catalyst solution contained an average of 1268 ppm of rhodium (range 1204–1374 ppm). The first 3100 ml. of the column effluent was discarded. The column was sampled periodically about one-third and two-thirds of the distance from the top, and at the bottom. Rhodium analyses and Gardner Color Numbers for the bottom effluent are given below (the volumes are corrected for the hexane originally present and liquid left on the column).

| ml. Through Column | Gardner Color | ppm Rhodium |
| --- | --- | --- |
| 650 | 6–7 | 37 |
| 1860 | 9 | 53 |
| 3040 | 12 | 115 |
| 5365 | 14–15 | 324 |
| 7740 | 16 | 492 |
| 9510 | 16–17 | 592 |
| 10,475 | 17 | 518 |

These results show about 76% of the rhodium was removed by the carbon. Analyses from the other sampling points shown that of the adsorbed rhodium, 76% was in the top third, 13% in middle third, and 11% in bottom third. A longer and/or wider column would have given an even better recovery.

I claim:
1. In a process for making 1,4-hexadiene from ethylene and 1,3-butadiene in the presence of a rhodium catalyst and of an organic liquid, the improvement of removing dissolved rhodium compounds from the organic, liquid process effluent by first contacting said effluent for at least about 0.1 hour with activated carbon of decolorizing grade, then separating it from the activated carbon.
2. The process of claim 1 wherein the organic, liquid effluent is water-extracted prior to the rhodium removal step.
3. The process of claim 1 wherein the contact time is 40–70 hours.
4. The process of claim 1 which is carried out continuously.
5. The process of claim 4 which is carried out in a column, the liquid being directed upward and the activated carbon bed being at intervals moved downward, fresh activated carbon being at intervals supplied from above, and spent activated carbon being removed from the bottom.
6. A process of claim 1 wherein the initial concentration of rhodium in the organic, liquid effluent is about 300–1800 parts per million.
7. A process of claim 1 wherein the temperature is maintained at about −20° to +120°C.
8. The process of claim 1 wherein rhodium trichloride is used as the catalyst in making 1,4-hexadiene.
9. The process of claim 8, wherein the contact time is 40–70 hours.
10. The process of claim 8, which is carried out continuously.
11. The process of claim 10 wherein the temperature is maintained at about −20° to +120°C.

* * * * *